(12) United States Patent
Van Berkel et al.

(10) Patent No.: US 9,063,047 B2
(45) Date of Patent: Jun. 23, 2015

(54) SYSTEM AND METHOD FOR EXTRACTING A SAMPLE FROM A SURFACE

(75) Inventors: Gary Van Berkel, Oak Ridge, TN (US); Thomas Covey, Richmond Hill (CA)

(73) Assignees: UT-Battelle, LLC, Oak Ridge, TN (US); DH Technologies Development PTE. LTD., UOB Plaza (SG)

( * ) Notice: Subject to any disclaimer, the term of this patent is extended or adjusted under 35 U.S.C. 154(b) by 0 days.

(21) Appl. No.: 13/102,606

(22) Filed: May 6, 2011

(65) Prior Publication Data

US 2011/0284735 A1 Nov. 24, 2011

Related U.S. Application Data

(60) Provisional application No. 61/332,486, filed on May 7, 2010.

(51) Int. Cl.
*H01J 49/00* (2006.01)
*G01N 1/40* (2006.01)
*B01L 3/00* (2006.01)
*G01N 1/02* (2006.01)

(52) U.S. Cl.
CPC .......... *G01N 1/4055* (2013.01); *B01L 3/502715* (2013.01); *G01N 2001/028* (2013.01); *H01J 49/00* (2013.01)

(58) Field of Classification Search
CPC ........ H01J 49/00; H01J 49/04; H01J 49/0431
USPC ................... 250/281, 282, 283, 284, 288
See application file for complete search history.

(56) References Cited

U.S. PATENT DOCUMENTS

| | | | | |
|---|---|---|---|---|
| 4,132,527 A * | 1/1979 | Maekawa et al. | ............... | 436/66 |
| 4,726,487 A * | 2/1988 | Mitri | ............... | 220/718 |
| 4,745,809 A | 5/1988 | Collins et al. | | |
| 4,840,912 A * | 6/1989 | Glattstein | ............... | 436/92 |
| 4,865,199 A * | 9/1989 | Zimmer | ............... | 206/515 |
| 5,205,473 A * | 4/1993 | Coffin, Sr. | ............... | 229/403 |
| 5,271,798 A | 12/1993 | Sandhu et al. | | |
| 5,783,938 A | 7/1998 | Munson et al. | | |
| 6,140,639 A | 10/2000 | Gusev et al. | | |

(Continued)

FOREIGN PATENT DOCUMENTS

| CN | 101484808 | 11/1999 |
|---|---|---|
| DE | 4200497 | 7/1993 |

(Continued)

OTHER PUBLICATIONS

Eskin, Just a Day at the Beach, Jun. 2, 2002, Chicago Tribune.*

(Continued)

*Primary Examiner* — Michael Logie
*Assistant Examiner* — Jason McCormack
(74) *Attorney, Agent, or Firm* — Novak Druce Connolly Bove + Quigg LLP

(57) ABSTRACT

A system and method is disclosed for extracting a sample from a sample surface. A sample is provided and a sample surface receives the sample which is deposited on the sample surface. A hydrophobic material is applied to the sample surface, and one or more devices are configured to dispense a liquid on the sample, the liquid dissolving the sample to form a dissolved sample material, and the one or more devices are configured to extract the dissolved sample material from the sample surface.

34 Claims, 14 Drawing Sheets

(56) References Cited

U.S. PATENT DOCUMENTS

| | | | |
|---|---|---|---|
| 6,290,863 B1 | 9/2001 | Morgan et al. | |
| 6,409,832 B2 | 6/2002 | Weigl et al. | |
| 6,478,238 B1 | 11/2002 | Wachs et al. | |
| 6,495,824 B1* | 12/2002 | Atkinson | 250/287 |
| 6,569,384 B2 | 5/2003 | Greenbaum et al. | |
| 6,803,566 B2 | 10/2004 | Van Berkel | |
| 6,864,480 B2* | 3/2005 | Staats | 506/33 |
| 7,270,948 B2 | 9/2007 | Demirev | |
| 7,445,907 B2 | 11/2008 | Everett et al. | |
| 7,525,105 B2 | 4/2009 | Kovtoun | |
| 7,718,958 B2 | 5/2010 | Shiea et al. | |
| 7,762,638 B2 | 7/2010 | Cruchon-Dupeyrat et al. | |
| 2002/0168778 A1* | 11/2002 | Andrien et al. | 436/173 |
| 2003/0049177 A1* | 3/2003 | Smith et al. | 422/100 |
| 2003/0166265 A1* | 9/2003 | Pugia et al. | 435/288.3 |
| 2003/0193020 A1* | 10/2003 | Van Berkel | 250/288 |
| 2004/0023410 A1 | 2/2004 | Stacey | |
| 2005/0087122 A1 | 4/2005 | Ismagliov et al. | |
| 2005/0116161 A1* | 6/2005 | Hafeman et al. | 250/282 |
| 2005/0178959 A1* | 8/2005 | Lopez-Avila et al. | 250/288 |
| 2005/0276937 A1* | 12/2005 | Kosth | 428/34.2 |
| 2007/0046934 A1 | 3/2007 | Roy | |
| 2007/0138384 A1* | 6/2007 | Keiser | 250/282 |
| 2007/0224697 A1 | 9/2007 | Park | |
| 2007/0259445 A1 | 11/2007 | Cedra | |
| 2007/0295902 A1 | 12/2007 | Shea et al. | |
| 2008/0128614 A1 | 6/2008 | Nikolaev et al. | |
| 2008/0131949 A1* | 6/2008 | Bortolin et al. | 435/173.9 |
| 2008/0230387 A1* | 9/2008 | McBride et al. | 204/451 |
| 2008/0272294 A1 | 11/2008 | Kovtoun | |
| 2008/0308722 A1 | 12/2008 | Shiea | |
| 2009/0000364 A1 | 1/2009 | Yu | |
| 2009/0053689 A1* | 2/2009 | Oviso et al. | 435/5 |
| 2009/0121124 A1* | 5/2009 | Schneider | 250/282 |
| 2009/0127454 A1* | 5/2009 | Ritchie et al. | 250/282 |
| 2009/0253210 A1* | 10/2009 | Kobold et al. | 436/63 |
| 2009/0263440 A1* | 10/2009 | Kendall | 424/412 |
| 2010/0038529 A1* | 2/2010 | Sato et al. | 250/282 |
| 2010/0047129 A1* | 2/2010 | LaStella et al. | 422/68.1 |
| 2010/0224013 A1* | 9/2010 | Van Berkel et al. | 73/863.81 |
| 2011/0100091 A1* | 5/2011 | Harrup et al. | 73/23.35 |
| 2011/0259205 A1* | 10/2011 | Delorme | 99/299 |
| 2012/0119079 A1* | 5/2012 | Ouyang et al. | 250/282 |
| 2012/0224013 A1* | 9/2012 | Liang | 347/105 |

FOREIGN PATENT DOCUMENTS

| | | |
|---|---|---|
| DE | 4207074 | 9/1993 |
| DE | 102004048380 | 4/2006 |
| DE | 102006056929 | 6/2008 |
| EP | 1252366 | 10/2002 |
| GB | 1272409 | 4/1972 |
| GB | 1451599 | 10/1976 |
| JP | 7159293 | 6/1995 |
| JP | 10148605 | 6/1998 |
| JP | H11304666 | 11/1999 |
| JP | 2003035671 | 2/2003 |
| JP | 2004184137 | 7/2004 |
| JP | 2005523456 | 8/2005 |
| JP | 2006059641 | 3/2006 |
| WO | 2007066518 | 6/2007 |
| WO | 2008038507 | 4/2008 |

OTHER PUBLICATIONS

Van Berkel, G.J.; Pasilis, S. P.; Ovchinnikova, O. "Established and Emerging Atmospheric Pressure Surface Sampling/Ionization Techniques for Mass Spectrometry." J. Mass Spectrom., 2008, 43, 1161-1180.

Van Berkel, Gary J. et al., "Thin-Layer Chromatography and Electrospray Mass Spectroscopy Coupled Using a Surface Sampling Probe," Anal. Chem. 2002, 74, pp. 6216-6223.

Keiji G. Asano et al., "Self-aspirating atmospheric pressure chemical ionization source for direct sampling of analytes on surfaces and in liquid solutions," Rapid Commun. Mass Spectrom. 2005, 19, pp. 2305-2312.

Becker et al., "Evidence of Near-Field Laser Ablation Inductively Coupled Plasma Mass Spectrometry (NF-LA-ICP-MS) at Nanometre Scale for Elemental and Isotopic Analysis on Gels and Biological Samples," Journal of Analytical Atomic Spectrometry, 2006, p. 19-25. vol. 21, The Royal Society of Chemistry.

Bohn et al., "Field Enhancement in Apertureless Near-Field Scanning Optcal Micoscopy"J. Opt. Soc. AM A/vol. 18, No. 12/Dec. 2001, p. 2998-3006, Optical Society of America.

Chapter 2, "Liquid-Phase Pulsed Laser Ablation".

Chen et al., "The Irradiation Effect of a Nd-YAG Pulsed on the CeO2 Target in the Liquid," Materials Letters, 2004, p. 337-341. vol. 58, Elsevier.

De Serio et al., "Lookng at the Nanoscale; Scanning Near Field Optical Microscopy." Trends in Analytical Chemistry, vol. 22, No. 2, 2003.

Douglas et al., "Laser Ablation of a Sample in Liquid—LASIL," J. Anal. At. Spectrom, 2011, The Royal Society of Chemistry.

Dunn, "Near-Field Scanning Optical Microscopy," Chem.Rev., 1999, p. 2891-2927. vol. 99.

Leung, et al., "Transmission Studies of Explosive Vaporization of a Transparent Lquid Film on an Opaque Solid Surface Induced by Excimer-Laser-Pulsed Irradiation," J. Appl. Phy., 1992, p. 2256-2263, vol. 72 No. 6.

M. Meunier, et al., "Laser Processing Laboratory. Colloidal Metal Nanoparticles Synthesized by Femtosecond Laser Ablation in Liquids," http://LPL.phys.polymtl.ca. Retrieved Mar. 8-10, 2005.

Muravitskaya et al., "Laser Ablation in Liquids as a New Technique of Sampling in Elemental Analysis of Solid Materials," Spectrochimica Acta part B, 2009, p. 119-125, vol. 64, Elsevier B.V.

Novotny et al., "Near-field Optical Microscopy and Spectroscopy with Pointed Probes" Annu. Rev. Phys. Chem., 2006, p. 303-331, vol. 57, Annual Reviews.

Reedy, "Solid Dispersions," last visited Oct. 19, 2011 and presented at http://www.authorstream.com/Presentation/robin_vinnu-623593-solid-dispersions/(video).

Schmid, et al., "Method for Modecular Nanoanalysis," CHIMIA 2006, 60, No. 11, pp. 783-788.

Schmitz, et al., "Towards Nanoscale Molecular Analysis at Atmospheric Pressure by a Near-Field Laser Ablation Ion Trap/Time-of-Flight Mass Spectrometer," Analytical Chemistry, 2008, p. 6537-6544, vol. 80 No. 17.

Stockle et al., "Nanoscale Atmospheric Pressure Laser Ablation-Mass Spectrometry," Analytical Chemistry, 2001, p. 1399-1402, vol. 73-7, American Chemical Society.

Tsuji et al., "Microsecond-Resolved Imaging of Laser Ablation at Solid-Liquid Interface: Investigation of Formation Process of Nano-Size Metal Colloids," Applied Surface Science 2004, p. 365-371, vol. 229, Elsevier B. V.

Yang, "Laser Ablation in Liquids: Applications in the Synthesis of Nanocrystals," Progress in Materials Science, 2007, p. 648-698, vol. 52, Elsevier.

Yasio, et al., "Laser Ablation in a Liquid Medium as a Technique for Solid Sampling." Journal of Analytical Atomic Spectrometry, Oct. 1991, vol. 6. p. 541-544.

Yasushi, "Apertureless Metalic Probes for Near-Field-Microscopy. Near-Field Optics and Surface Plasmon Polaritons," Topics Appl. Phys.81, 29-48 (2001).

Yavas et al., "Optical Reflectance and Scattering Studies of Nucleation and Growth of Bubbles at a Liquid-Solid Interface Induced by Pulsed Laser Heating," Physical Review Letters. 1993, p. 1830-1833, vol. 70, No. 12, The American Physical Society.

Yavas et al., "Bubble Nucleation and Pressure Generation During Cleaning Surfaces," Appl. Phys. A 64, 331-339 (1997).

Zeisel et al., "Pulsed Laser-Induced Desorption and Optical Imaging on a Nanometer Scale with Scanning Near-Field Microscopy using Chemically Etched Fiber Tips," Appl. Phys. Letter 1996, p. 2491-2, vol. 68 No. 18, Amer. Inst. of Physics.

(56) References Cited

OTHER PUBLICATIONS

Zijie et al., "Hollow Nanoparticle Generation on Laser-Induced Cavitation Bubbles via Bubble Interface Pinning," Applied Physical Letters, 2010, p. 124106-1-3. vol. 97, Amer. Inst. of Physics.

Zoriy et al., "Possibility of Nano-Local Element Analysis by Near-Field Laser Ablation Inductively Coupled Plasma Mass Spectrometry (LA-ICP-MS): New Experiment Arrangement and First Application," International Journal of Mass Spectrometry, 2008, p. 151-155, vol. 273, Elsevier B.V.

International Search Report mailed Jan. 12, 2011. In corresponding PCT patent application No. PCT/US2011/053799.

International Search Report mailed Mar. 12, 2012. In corresponding PCT patent application No. PCT/US2011/054622.

International Search report mailed Jan. 12, 2011. In corresponding PCT patent application No. PCT/US2011/035604.

Wu et al., "Particle detection by electrical impedance spectroscopy with asymmetric-polarization ac electroosmotic trapping", Microfluid Nanofluid (Apr. 6, 2005) 1: 161-167. (abstract only).

Zhang et al., "High-Throughput Microfabricated CE/ESI-MS: Automated Sampling from a Microwell Plate", Analytical Chemistry (Jun. 1, 2001) 73(11): 2675-2681. (abstract only).

* cited by examiner

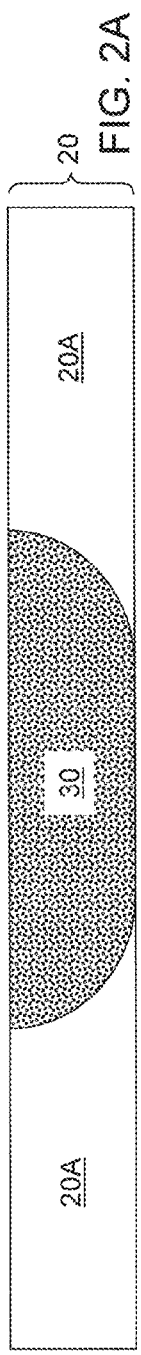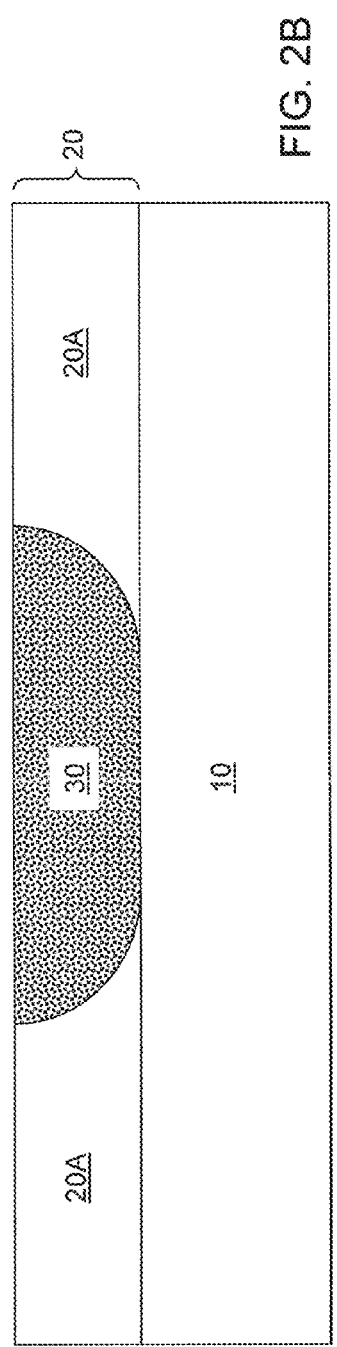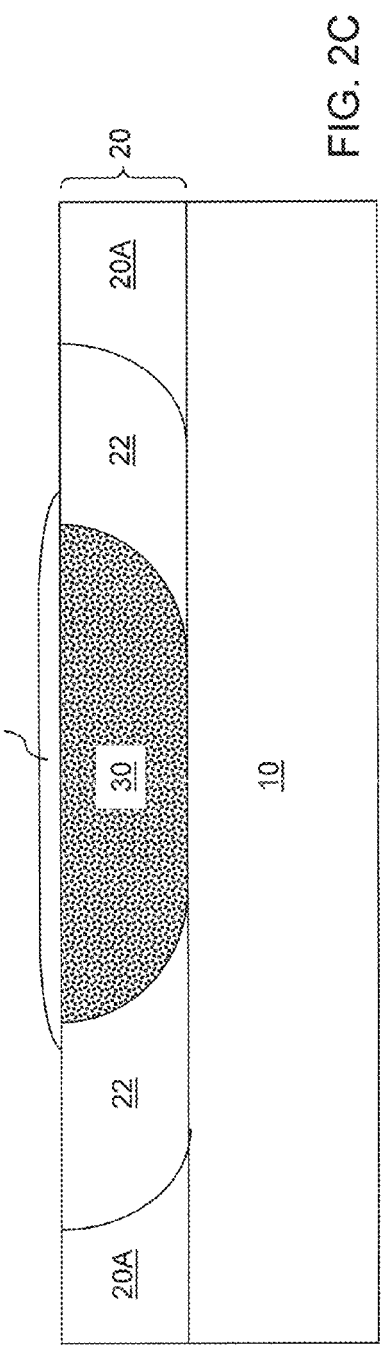

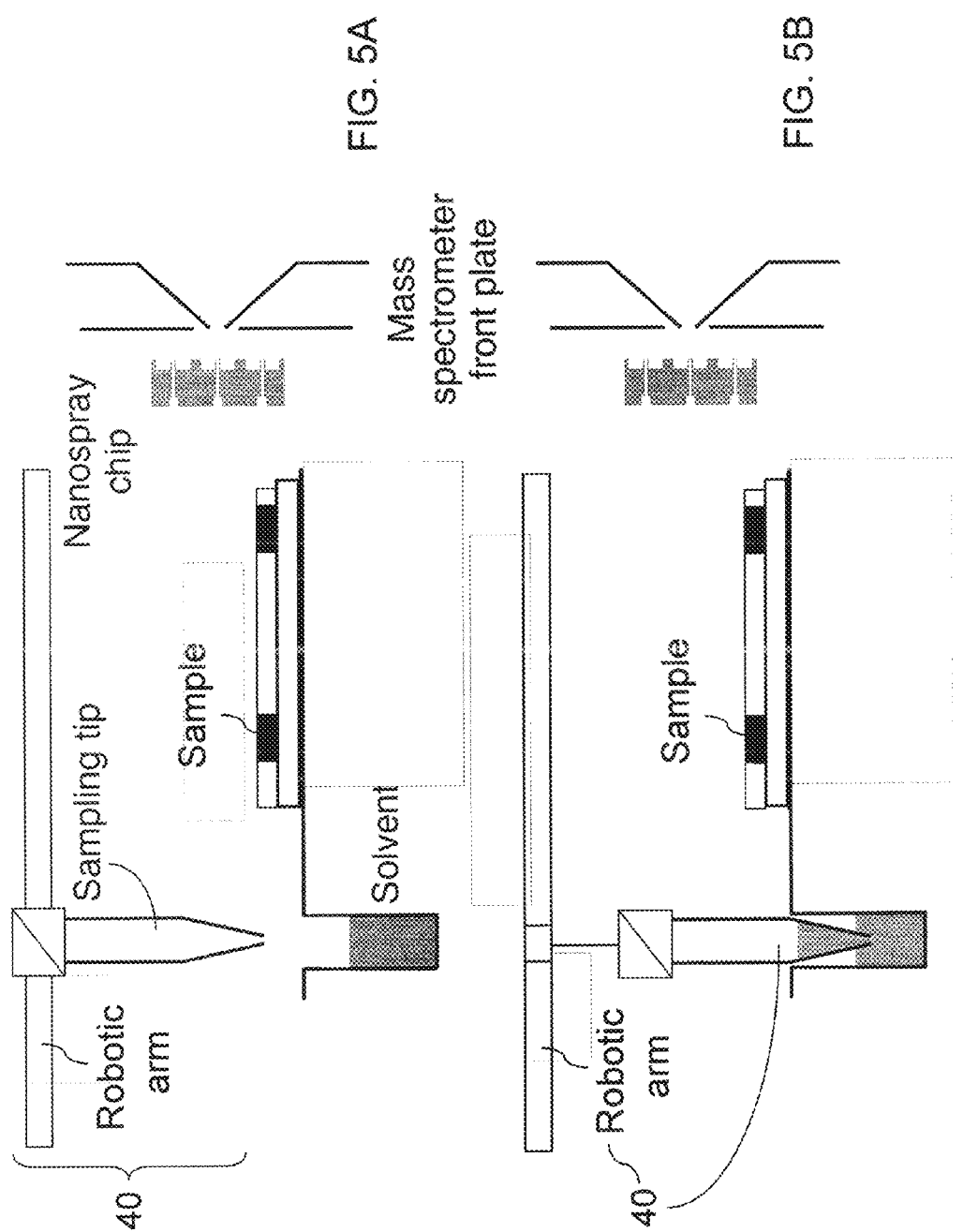

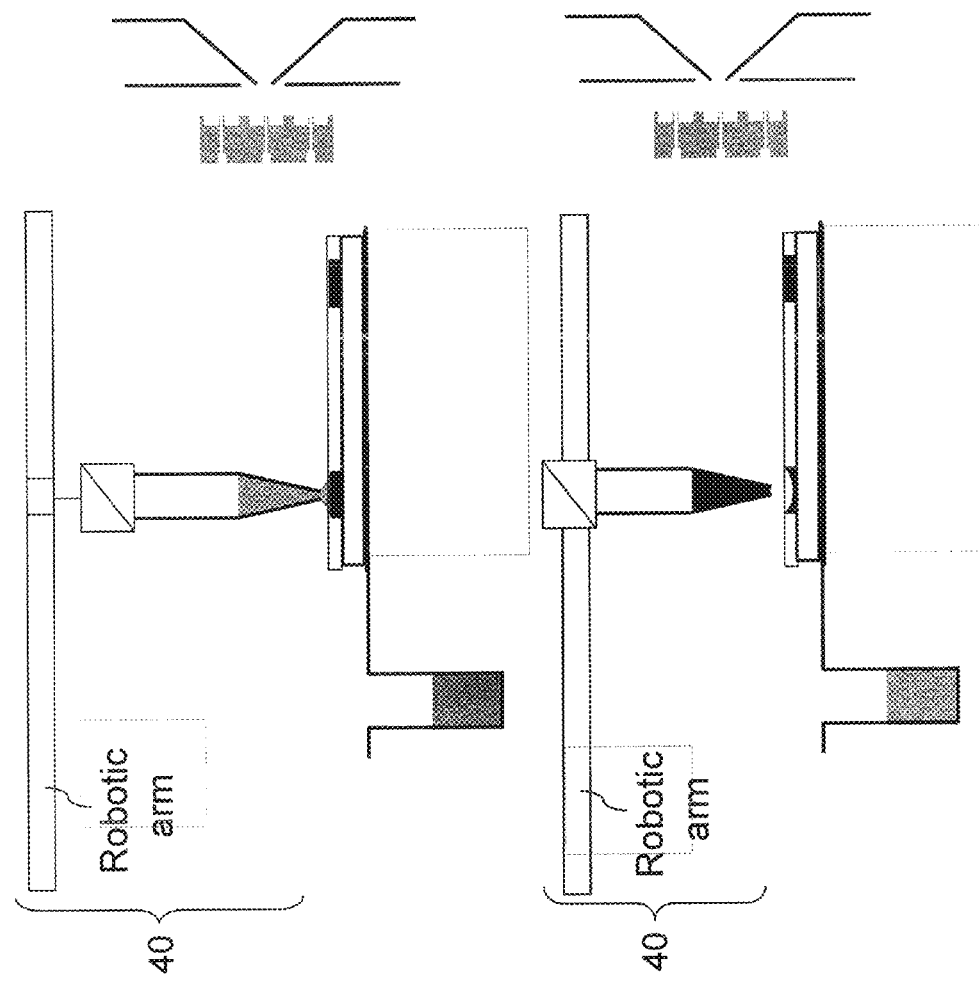

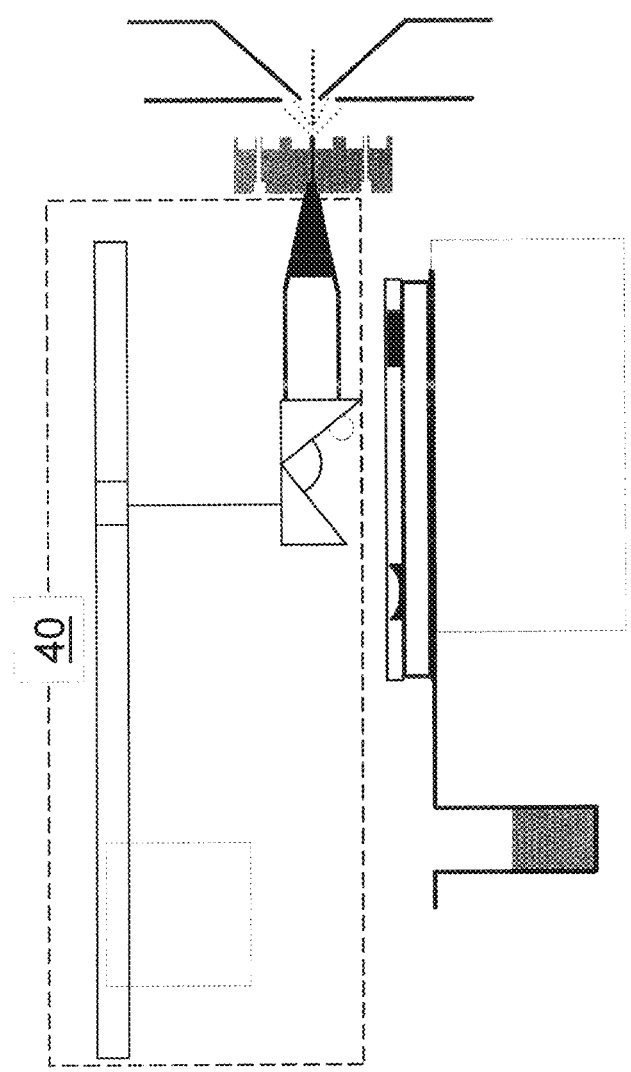

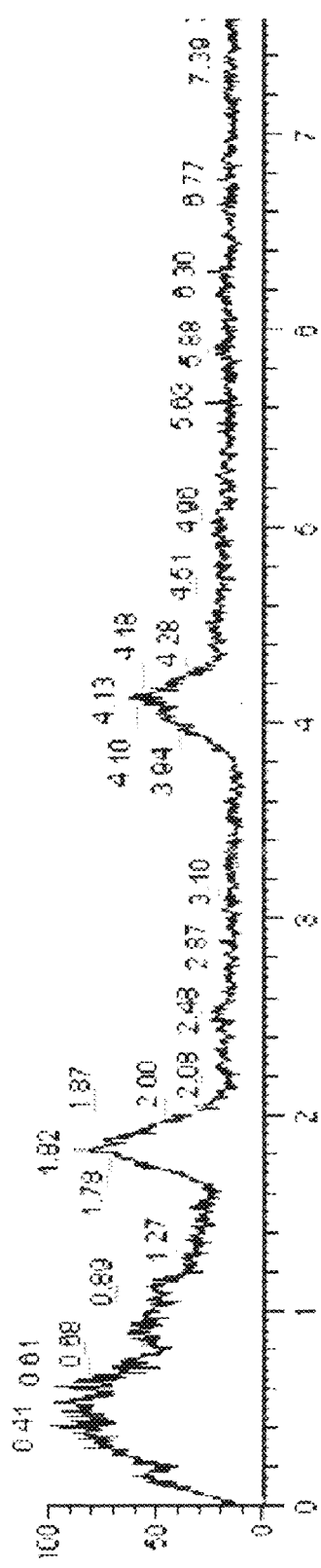
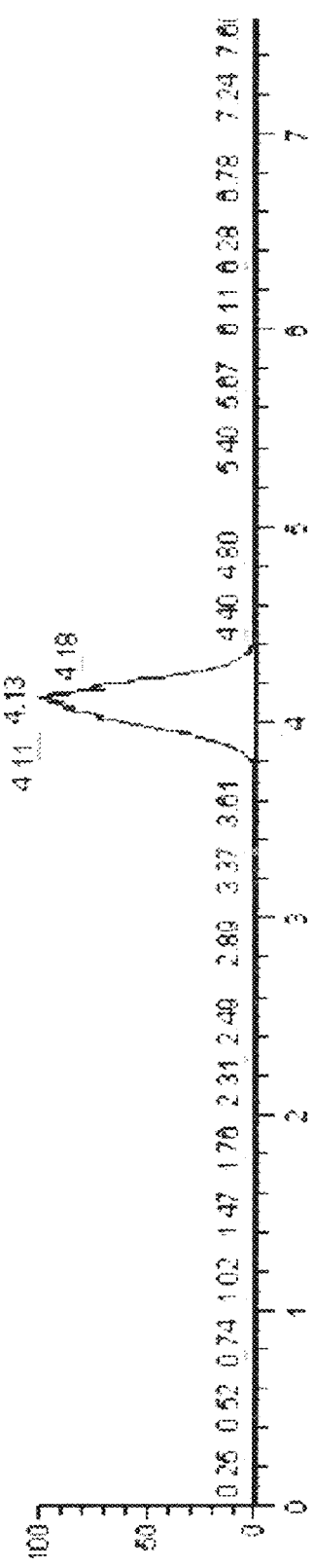
FIG. 9A
FIG. 9B

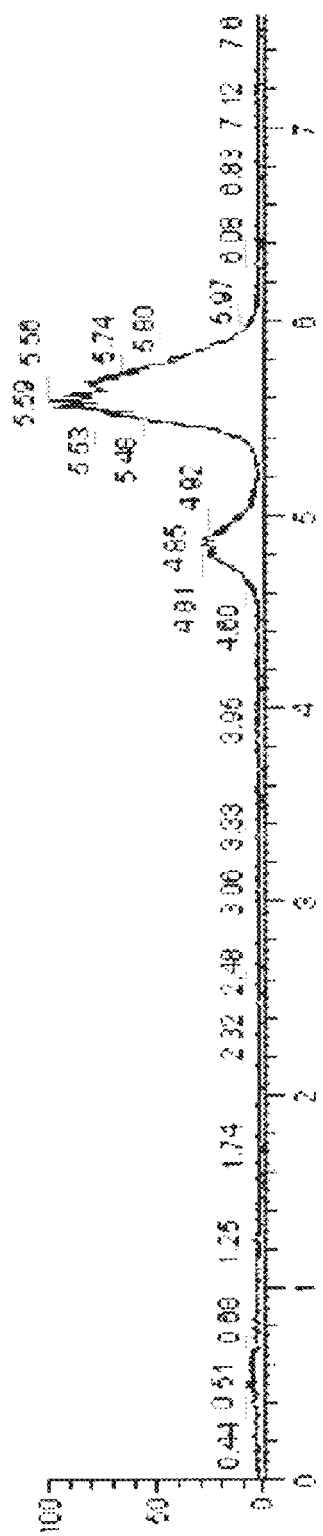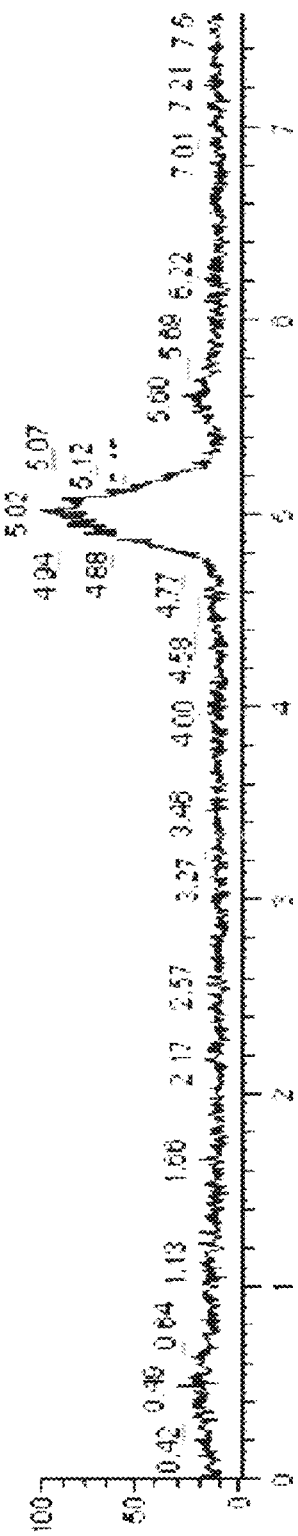
FIG. 9C
FIG. 9D

SYSTEM AND METHOD FOR EXTRACTING A SAMPLE FROM A SURFACE

CROSS REFERENCE TO RELATED APPLICATIONS

This application claims priority to U.S. Provisional Patent Application No. 61/332,486, filed May 7, 2010, entitled SYSTEM AND METHOD FOR EXTRACTING A SAMPLE FROM A SURFACE, the entire contents of which are incorporated herein by reference.

STATEMENT REGARDING FEDERALLY SPONSORED RESEARCH OR DEVELOPMENT

The applicant's teachings were made with government support under Contract No. DE-AC05-00OR22725 awarded by the U.S. Department of Energy. The government has certain rights in the applicant's teachings.

FIELD

The applicant's teachings relate to an apparatus and method for extracting a sample from a surface for analysis by mass spectrometry.

INTRODUCTION

Many types of atmospheric pressure surface analysis techniques have been developed for mass spectrometric detection. Typically, these techniques desorb or remove analytes from a solid surface by one mechanism and ionize them by another. Thermal desorption in the form of hot gases (ASAP, DART), laser (MALDI), or IR radiation is one means to desorb analytes. Acoustic desorption in the form of high frequency vibrations is another technique to desorb analytes. Solvent extraction by various means is yet another technique which includes bouncing nebulized droplets off a surface (DESI), establishing a liquid junction on a surface confined by surface tension forces (SSP), or by forming a mechanical seal on the surface to confine the liquid such as would be achieved with "o"-rings (Van Berkel, G. J.; Pasilis, S. P.; Ovchinnikova, O. "Established and Emerging Atmospheric Pressure Surface Sampling/Ionization Techniques for Mass Spectrometry." J. Mass Spectrom., 2008, 43, 1161-1180.) Ionization of the desorbed analytes is typically achieved by some variation of either chemical ionization or electrospray ionization by all of the above mentioned techniques.

Liquid extraction desorption techniques are the least destructive to analyte molecules because the amount of energy deposited into the system is minimized. An extraction solvent is brought in contact with a surface in order to dissolve the sample adhering to the surface. Hydrophilic surfaces will adsorb, dissipate, and retain hydrophilic solvents not allowing the analytes to be effectively removed and ionized for mass spectrometric detection.

There are many important hydrophilic solid materials used for the sampling and storage of aqueous based samples such as biological fluids and environmental samples. Cellulose or paper based substrates are widely used because of their adsorptive properties and chemical stability in the dry state. Hydrophilic surfaces such as these are very difficult to directly analyze with a mass spectrometer by liquid extraction desorption techniques because the liquid remains in the paper. Indirect analysis can be done but it adds extra tests in the process and is laborious and time consuming. Typically, the region of the paper that contains the sample is physically excised followed by addition of large volumes of solvent, filtration and centrifugation steps. Also, when high spatial resolution is required physical excision can blur the boundaries.

SUMMARY

In accordance with an aspect of the applicant's teachings, a system is provided for extracting a sample from a sample surface. A sample is provided, and a sample surface receives the sample which is deposited on the sample surface. A hydrophobic material is applied to the sample surface and one or more devices are configured to dispense a liquid on the sample, the liquid dissolving the sample to form a dissolved sample material, and the one or more devices are configured to extract the dissolved sample material from the sample surface. In various embodiments, the sample surface comprises an absorptive layer which can be a hydrophilic material. The absorptive layer can be selected from a group consisting of paper, fabric, porous ceramic material and a combination thereof. In various aspects, a substrate provides mechanical support to the absorptive layer. In various embodiments, the hydrophobic material is selected from a group consisting of silicone, fluorinated alkane, and waxes. The hydrophobic material can comprise patterns in the absorptive layer of the sample surface forming sample wells prior to depositing the sample. In various aspects, the system further comprises hydrophobic barriers and moats to contain overflow of the sample from the sample wells. In various aspects, a hydrophobic layer can form over the region of the absorptive layer containing the sample. The hydrophobic material can comprise a solid phase at 293.15 K. In various embodiments, the sample can be embedded in the absorptive layer, and it can comprise a biological material, such as blood or tissue. In various aspects, the liquid can comprise a solvent that dissolves the sample. The one or more devices can comprise a liquid extraction surface sampling probe or a robotic arm configured to move a pipette tip to and away from the sample. In various embodiments, the one or more devices can comprise providing a charged pneumatically generated spray to create charged droplets that can extract the dissolved sample material from the sample surface. In various embodiments, the system further comprises ionizing the extracted dissolved sample material with an electrospray ionization device, an atmospheric chemical ionization device, an inductively coupled plasma ionization device, or an atmospheric photo ionization device. The ionized dissolved sample material can be analyzed by a mass spectrometer.

In another aspect, a method is provided for extracting a sample from a sample surface. A sample is provided, and a sample surface receives the sample which is deposited on the sample surface. A hydrophobic material is applied to the sample surface and one or more devices are configured to dispense a liquid on the sample, the liquid dissolving the sample to form a dissolved sample material, and the one or more devices are configured to extract the dissolved sample material from the sample surface. In various embodiments, the sample surface comprises an absorptive layer which can be a hydrophilic material. The absorptive layer can be selected from a group consisting of paper, fabric, porous ceramic material and a combination thereof. In various aspects, a substrate provides mechanical support to the absorptive layer. In various embodiments, the hydrophobic material is selected from a group consisting of silicone, fluorinated alkane, and waxes. The hydrophobic material can comprise patterns in the absorptive layer of the sample surface forming sample wells prior to depositing the sample. In various aspects, the method further comprises hydrophobic barriers and moats to contain overflow of the sample from the sample wells. In various aspects, a hydrophobic layer can form over the region of the absorptive layer containing the sample. The hydrophobic material can comprise a solid phase at 293.15 K. In various embodiments, the sample can be embedded in the absorptive layer, and it can comprise a biological material, such as blood or tissue. In various aspects, the liquid can comprise a solvent that dissolves the sample. The one or more devices can comprise a liquid extraction surface sampling probe or a robotic arm configured to move a pipette tip to and away from the sample. In various embodiments, the one or more devices can comprise providing a charged pneumatically generated spray to create charged droplets that can extract the dissolved sample material from the sample surface. In various embodiments, the method further comprises ionizing the extracted dissolved sample material with an electrospray ionization device, an atmospheric chemical ionization device, an inductively coupled plasma ionization device, or an atmospheric photo ionization device. The ionized dissolved sample material can be analyzed by a mass spectrometer.

BRIEF DESCRIPTION OF THE DRAWINGS

The skilled person in the art will understand that the drawings, described below, are for illustration purposes only. The drawings are not intended to limit the scope of the applicant's teachings in anyway.

FIG. 2A schematically illustrates a vertical cross-section of an absorptive layer comprising a sample in accordance with various embodiments of the applicant's teachings.

FIG. 2B schematically illustrates a vertical cross-sectional view of an adsorptive layer comprising a sample on a substrate prior to application of a hydrophobic material in accordance with various embodiments of the applicant's teachings.

FIG. 2C schematically illustrates a vertical cross-sectional view of an adsorptive layer comprising a sample on a substrate after application of a hydrophobic material in accordance with various embodiments of the applicant's teachings.

FIG. 5A-5E schematically illustrate sequential side views of an experimental set-up employing a pipette and a robotic arm sampling paper containing blood spot samples in accordance with various embodiments of the applicant's teachings.

FIG. 9A shows a time-dependent readout at m/z setting of 190 (corresponding to hydrastinine) from a liquid microjunction surface sample probe scan of a post-development treated normal phase HPTLC plate obtained from chromatography on a sample of goldenseal root extract coated with a hydrophobic material in accordance with various embodiments of the applicant's teachings.

FIG. 9B is a time-dependent readout at m/z setting of 384 (corresponding to hydrastine) from the liquid microjunction surface sample probe scan of the post-development treated normal phase HPTLC plate obtained from chromatography on a sample of goldenseal root extract coated with a hydrophobic material in accordance with various embodiments of the applicant's teachings.

FIG. 9C is a time-dependent readout at m/z setting of 338 (corresponding to jatrorrhizine) from the liquid microjunction surface sample probe scan of the post-development treated normal phase HPTLC plate obtained from chromatography on a sample of goldenseal root extract coated with a hydrophobic material in accordance with various embodiments of the applicant's teachings.

FIG. 9D is a time-dependent readout at m/z setting of 352 (corresponding to berberastine) from the liquid microjunction surface sample probe scan of the post-development treated normal phase HPTLC plate obtained from chromatography on a sample of goldenseal root extract coated with a hydrophobic material in accordance with various embodiments of the applicant's teachings.

DESCRIPTION OF VARIOUS EMBODIMENTS

Figure 1A:
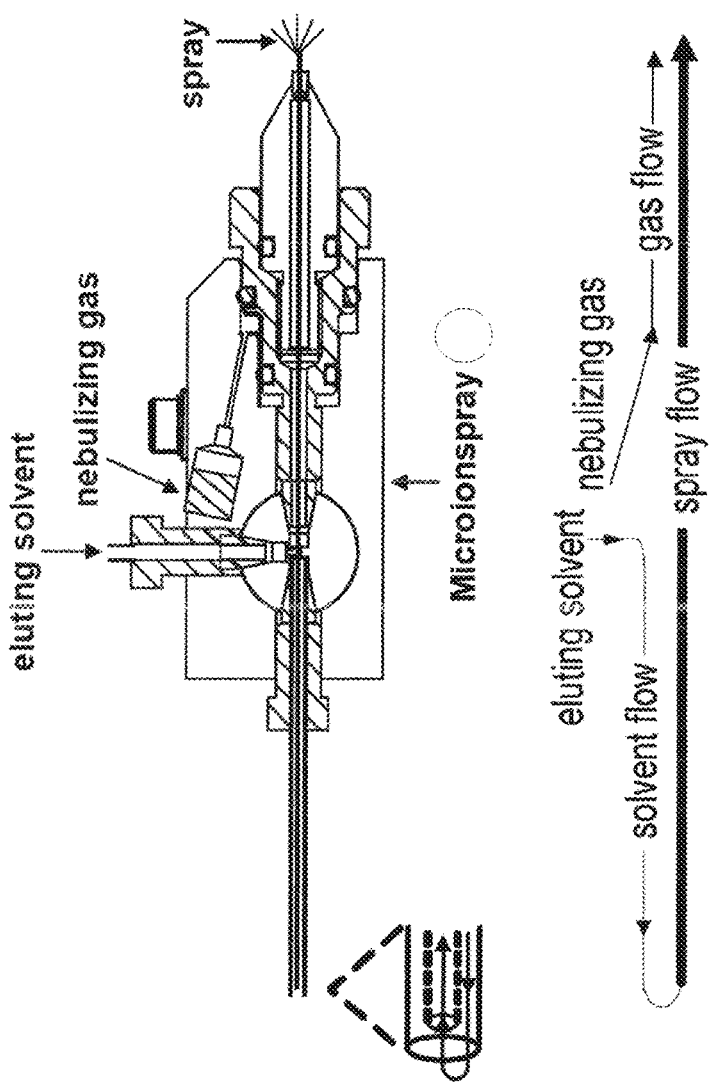
FIG. 1A schematically illustrates a cross-sectional view of a prior art microionspray device including a liquid microjunction surface sampling probe and the fluid flow paths in the microionspray device in accordance with various embodiments of the applicant's teachings.

It is noted that like and corresponding elements mentioned herein and illustrated in the drawings are referred to by like reference numerals. It is also noted that proportions of various elements in the accompanying figures are not drawn to scale to enable clear illustration of elements having smaller dimensions relative to other elements having larger dimensions.

It should be understood that the phrase "a" or "an" used in conjunction with the applicant's teachings with reference to various elements encompasses "one or more" or "at least one" unless the context clearly indicates otherwise.

Figure 1B:
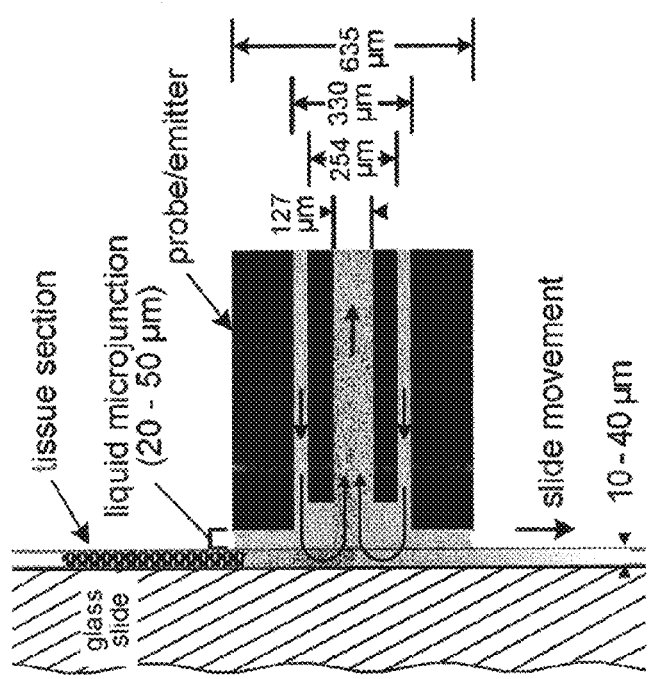
FIG. 1B schematically illustrates a cross-sectional view of a proximal end of a prior art liquid microjunction surface sampling probe in accordance with various embodiments of the applicant's teachings.

Reference is made to FIG. 1A which schematically illustrates a cross-sectional view of a prior art microionspray device including a liquid microjunction surface sampling probe and the fluid paths in the microionspray device. Referring to FIG. 1B, a cross-sectional view of a proximal end of a prior art liquid microjunction surface sampling probe is shown. Before the operation of a liquid microjunction surface sampling probe, which is also referred to as an "emitter," a proximal end of the liquid microjunction surface sampling probe is brought in proximity to a surface of a sample. The distance between the proximal end of the liquid microjunction surface sampling probe and the surface of the sample is maintained at a distance that enables formation of a liquid microjunction interface. The distance can be typically from 20 microns to 50 microns.

A liquid, which is referred to as an eluting solvent or an eluent, is pumped toward a surface of a sample through an annulus of a solvent delivery capillary located within a probe or an "emitter." The liquid flow toward the sample is referred to as solvent flow. The sample can be any material that can be dissolved in the eluting solvent. For example, the sample can be a thin tissue section having a thickness from 5 microns to 100 microns. The sample can be mounted to a substrate such as a glass slide. The eluting solvent can form a liquid microjunction with the surface of the sample, which is effected by holding the proximal end of the liquid microjunction surface sampling probe within a distance sufficient to maintain the liquid microjunction interface from the sample surface.

Materials from the surface of the sample can be dissolved in the eluting solvent. The mixture of the eluting solvent and the dissolved materials is referred to as an eluate, which is aspirated from the surface of the sample through an inner sampling capillary that is surrounded by the annular solvent delivery capillary. The flow of the eluate from the sample surface is referred to as spray flow. The spray flow can be directed into an atmospheric pressure ion source of a mass spectrometer. FIG. 1B shows a set of dimensions for a proximal end of a coaxial liquid microjunction surface sampling probe.

Additional details of liquid extraction surface sampling probes are provided in Gary J. Van Berkel et al., "Thin-Layer Chromatography and Electrospray Mass Spectroscopy Coupled Using a Surface Sampling Probe," Anal. Chem. 2002, 74, pp. 6216-6223; Keiji G. Asano et al., "Self-aspirating atmospheric pressure chemical ionization source for direct sampling of analytes on surfaces and in liquid solutions," Rapid Commun. Mass Spectrom. 2005, 19, pp. 2305-2312; and U.S. Pat. No. 6,803,566 to Gary J. Van Berkel.

Because a microjunction interface is laterally exposed when a liquid microjunction surface sampling probe is employed, the eluting solvent is continuously fed to the periphery of a microjunction interface. When a surface is an absorbent layer, i.e., as in the case of a piece of paper or a piece of fabric in which the sample, such as blood is embedded, the eluting solvent is continuously absorbed at the periphery of the microjunction interface, disrupting the microjunction and making retrieval or extraction of the liquid and sample from the surface impossible as the eluate spreads throughout the surface. Other forms of liquid extractions, such as sprayed droplets or attempts at mechanical seals, will suffer a similar fate; the affinity of the hydrophilic liquid for the hydrophilic surface will cause the liquid to adsorb into and migrate through the surface material making it no longer available for a measurement by direct analysis.

Hydrophobic surfaces will promote the formation of surface tension barriers at the interface of hydrophilic solvents. In this situation, provided the surface is not excessively hydrophobic preventing any penetration of the solvent, the droplets will maintain their integrity held intact by surface tension at the edges and still allow sufficient contact at and below the surface to extract sample. However, in order to allow the extraction solvent and the surface on which the sample is deposited to be effectively separated they must have dissimilar properties.

The applicant's teachings relate to the desorption and dissolution of a sample from a surface by liquid extraction mechanisms. The applicant's teachings can allow for the direct analysis of a wide variety of surfaces with a wide variety of solvents and, in particular, can allow for the direct analysis of hydrophobic surfaces with hydrophilic solvents.

Referring to FIG. 2A, in various embodiments in accordance with the applicant's teachings, a sample surface for depositing a sample on the sample surface comprises an absorptive layer 20 that can have an absorptive portion 20A. In various embodiments, the sample can be embedded in the absorptive portion 20A. The absorptive portion 20A can be free of foreign material and can comprise a layer that can absorb a fluid. The sample can be deposited and can be embedded on the absorptive portion 20A of the absorptive layer 20 of the sample surface, as shown in region 30 of FIG. 2A. In various aspects, the absorptive layer 20 of FIG. 2A can be prepared, for example, by providing a pristine absorptive layer consisting of the foreign-material-free absorptive portion 20A. Upon exposure of a portion of the foreign-material-free absorptive portion 20A to a sample material in the form of a fluid, the fluid can be absorbed or adsorbed to the foreign-material-free absorptive portion 20A, forming the sample region 30 comprising the fluid. Since the pristine absorptive layer as provided can have a porous structure before formation of the sample region 30, the absorptive layer 20, comprising the sample region 30 and the foreign-material-free absorptive portion 20A, also can include a porous structure which can allow the sample material to be adsorbed in the sample region 30.

In various embodiments, the absorptive layer 20 can comprise a piece of paper, a piece of cloth, a porous ceramic material, or a combination thereof. The absorptive layer 20 can comprise, but is not limited to, a hydrophilic material. The thickness of the absorptive layer 20 can be, for example, from about 100 microns to about 10 mm, although as will be appreciated by those of skill in the art, lesser and greater thicknesses can also be employed.

Referring to FIG. 2B, in various embodiments in accordance with the applicant's teachings, the absorptive layer 20 can be disposed on a top surface of a substrate 10. The substrate 10 can be a structure that provides mechanical support to the absorptive layer 20. As such, use of the substrate 10 is optional when the absorptive layer 20 alone provides sufficient mechanical support during subsequent analysis of the sample region 30. If the absorptive layer 20 does not provide sufficient mechanical strength to withstand subsequent analysis on the sample region 30, for example, as in the case of a thin paper tissue including a sample material, the substrate 10 can provide mechanical support to the absorptive layer 20.

The top surface of the substrate 10 can contact the back side surface of the absorptive layer 20. In various aspects, the top surface of the substrate can be a hydrophobic surface. The combination of the absorptive layer 20 and the substrate 10 is herein referred to as a sample assembly (10, 20). The substrate 10 can include a metallic material, an insulator material, or any other rigid material provided that the substrate 10 can provide sufficient mechanical support during subsequent analysis of the embedded sample material in the sample region by liquid extraction methods. In various embodiments, the sample region 30 can be formed within the absorptive layer 20 prior to bringing the absorptive layer 20 into contact with the substrate 10. In various embodiments, the absorptive layer 20 can be brought into contact with the substrate prior to formation of the sample region 30 by exposure to a sample material.

Referring to FIG. 2C, in various embodiments in accordance with the applicant's teachings, a hydrophobic material can be applied to the absorptive layer 20, of the sample surface, which contains the sample 30. In various embodiments, the hydrophobic material can be applied by spray coating around and on top of the sample region 30. In various embodiments, the hydrophobic material can be applied to the entirety of the absorptive layer 20, for example, by immersion or by spin coating.

In various embodiments, a hydrophobic material can be applied, for example, by spraying or dipping onto an absorptive layer having regions where samples have been previously deposited, which may include, but is not limited to, a biological sample or a chemical sample. The hydrophobic material can be embedded throughout the absorptive layer around the sample region to form a hydrophobic barrier peripheral to the sample preventing lateral diffusion of the extraction solvent and sample. The portion of the hydrophobic material applied over the sample region can form a thin and thus porous hydrophobic layer. Liquid extraction of the analyte molecules in the sample can occur through the porous hydrophobic barrier but the liquid can be confined by the continuous hydrophobic barrier peripheral to the sample.

In various embodiments, the hydrophobic material can be impregnated into the adsorptive layer prior to adding the sample. Patterned regions of hydrophobic barriers and undercoatings surrounding hydrophilic adsorptive areas for samples can confine the extraction liquid in a similar fashion to a non-patterned approach.

After application of the hydrophobic material, the sample assembly (10, 20) can be dried to allow volatile components of the sprayed material to evaporate. In various aspects, the drying period, for example, can be, but is not limited to, from about 1 minute to about 24 hours. The applied hydrophobic material can form a hydrophobic peripheral portion 22, which can comprise a hydrophobic material which can be embedded and can laterally confine the sample region 30. The entire periphery of the sample region 30 can be laterally surrounded by the hydrophobic peripheral portion 20. For example, in the case of a sample spot in a two-dimensional sheet, or two sides of the sample region 30 can be laterally contacted by two disjoined hydrophobic peripheral portions 20, for example, as in the case of a sample band in a strip such as a HPTLC plate. The hydrophobic peripheral portion 22 can be formed as the applied hydrophobic material can be embedded in an absorptive portion 20A contacting the sample region 30. The absorptive portion 20 A can be substantially free of foreign material or it can comprise low foreign material.

A hydrophobic layer 32 can be formed over the sample region 30. The hydrophobic layer 32 can be much thinner than the hydrophobic barrier 22 formed in the adsorbent material where no sample is present because sample has already saturated the adsorptive material. The thinness of layer 32 can be thinner than the thick deeply penetrating barrier formed at 22 because he sample has already saturated this area of the adsorptive material. The hydrophobic layer 32 can comprise the same material as the embedded hydrophobic material in the hydrophobic peripheral portion 22 but because it is much thinner, it has a degree of porosity allowing the solvent to penetrate into the sample while maintaining the property of preventing rapid and uncontrolled diffusion of the liquid throughout the adsorbent layer.

The treatment of the absorptive layer 20 by application of the hydrophobic material can reduce the wettability of the surface of the absorptive layer 20 so that an extraction liquid or sprayed droplets do not diffuse into the non-sample portion of the layer. The hydrophobic peripheral portion 22 immediately adjacent to the sample can inhibit the radial elution of analyte and extraction solvent from the sample region 30 within the absorptive layer 20.

In various aspects, the treatment of the absorptive layer 20 does not disrupt the spatial distribution of the embedded sample material within the sample region 30. In various aspects, the treatment of the absorptive layer 20 can allow the embedded sample material within the sample region 30 to be dissolved and extracted from the surface of the absorptive layer 20 during the operation of a liquid extraction. In various aspects, the treatment of the absorptive layer 20 does not contribute to a detrimental matrix effect, i.e., it does not result in ion suppression or inhibit analyte extraction from the surface.

An example of a suitable hydrophobic material that can be applied to the absorptive layer 20 of the sample surface can be silicone. A commercially available source of silicone can be a silicone spray that can typically be employed as a lubricant or as a water proofing agent.

Upon application onto the absorptive layer 20, silicone forms the hydrophobic peripheral portion 22 and the hydrophobic layer 32, which can impart hydrophobic character to the surface and the ability to form a stable liquid/solid interface. The thin silicone layer over the sample can have a degree of porosity allowing the extraction solvent to penetrate, dissolve the sample, and be withdrawn without dispersing and diffusing throughout the absorbent layer. The thick layer at 22 can be impermeable to the extraction solvent. Commercially available silicone sprays can include, but are not limited to, Carfa Magic Trio™ and Kiwi Camp Dry™.

Other examples of suitable hydrophobic materials that can be applied to the absorptive layer 20 of the sample surface are alkanes and fluorinated alkanes. Alkanes and fluorinated alkanes in the form of solids, liquids, or aerosols are often referred to as waxes, and can be applied to the surface by melting, painting, or spraying. Materials of this type can provide the option to pattern the adsorptive material defining regions that can comprise sample wells where samples can be deposited. The volume of the adsorptive sample well to be extracted by liquid can be controlled, and the extracted sample can be directly analyzed by atmospheric pressure ionization mass spectrometry.

Other reagents that can form a chemical bond instead of forming a physical association can also be employed provided that such reagents can form the hydrophobic peripheral portion 22 and optionally the hydrophobic layer 32 to render at least a portion of the top surface of the absorptive layer 20 hydrophobic.

The hydrophobic material can be in a solid phase at the operating temperature of the liquid extraction surface sampling probe. In various embodiments, the hydrophobic material can be in a solid phase at 293.15 K, i.e., at room temperature.

Figure 3A:
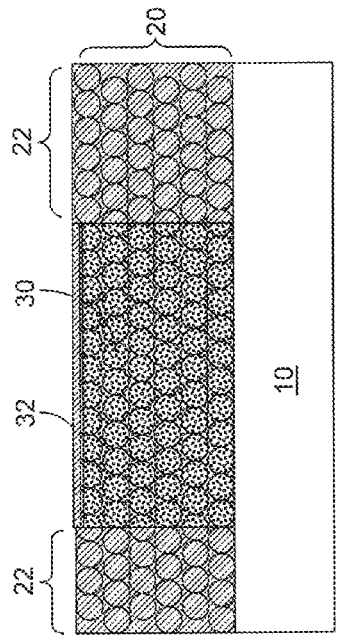
FIG. 3A schematically illustrates a cross-sectional view of a hydrophilic adsorptive layer comprising a sample prior to application of a hydrophobic material in accordance with various embodiments of the applicant's teachings.

Referring to FIG. 3A, in various embodiments according to the applicant's teachings, a schematic cross-sectional view of the sample assembly (10, 20) is shown prior to application of a hydrophobic material. The sample can be added to the adsorptive material in region 30. This step corresponds to the processing step of FIG. 2B. The porosity of the absorptive layer 20 is schematically illustrated by circles. In various embodiments, the embedded sample material of the sample region 30 can be located between structural units, such as a fiber, of the absorptive layer 30. In various embodiments, the embedded sample material of the sample region 30 can permeate into each structural unit, such as a fiber, of the absorptive layer 30.

Figure 3B:
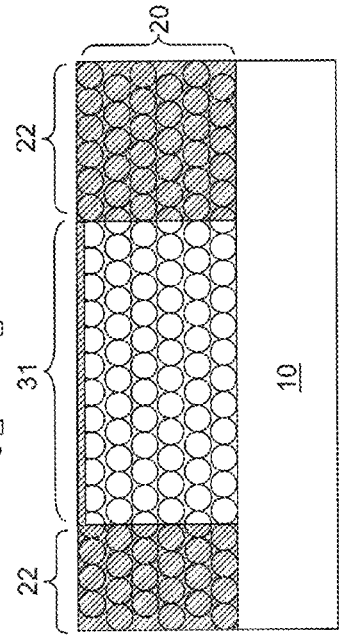
FIG. 3B schematically illustrates a cross-sectional view of a hydrophilic adsorptive layer comprising a sample followed by application of a hydrophobic material in accordance with various embodiments of the applicant's teachings.

Referring to FIG. 3B, in various embodiments according to the applicant's teachings, a schematic cross-sectional view of the sample assembly (10, 20) is shown after application of a hydrophobic material. This step corresponds to the processing step of FIG. 2C. A thin, porous hydrophobic layer 32 can cover the sample.

Figure 3C:
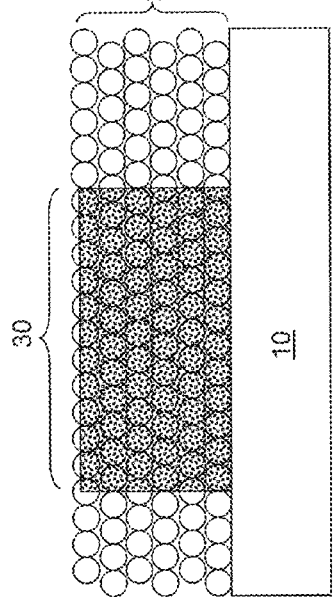
FIG. 3C schematically illustrates a cross-sectional view of the hydrophobic treated surface and sample and a proximal end of a liquid microjunction surface sampling probe during the operation of the sampling probe in accordance with various embodiments of the applicant's teachings.

Referring to FIG. 3C, in various embodiments according to the applicant's teachings, at least one device 40 can be brought to the top surface of the sample assembly (10, 20). The at least one device 40 can be configured to dispense a liquid onto the sample assembly and to extract the liquid from the sample assembly. The thin hydrophobic layer can allow solvent to penetrate and be extracted but inhibits excessive spreading across the surface. The at least one device 40 can be a single device that dispenses and extracts the liquid, or it can be a plurality of devices comprising a first device that can dispense the liquid and a second device that can extract the liquid.

In various embodiments, at least one device 40 can be a liquid extraction surface sampling probe. In various embodiments, the liquid extraction surface sampling probe can be brought into proximity with the sample region 30. In various aspects, a liquid can be fed to the sample region 30, for example, through an annular capillary. Typically, the liquid can be a solvent that can be capable of dissolving the sample embedded in region 30. The liquid is referred to as an eluting solvent or an eluent. The liquid in the sample region 30 can dissolve the embedded sample in region 30. The sample region 30 during the dissolution of the embedded material by the presence of the liquid is herein referred to as a dissolving sample region 34. The liquid that passes through an inner capillary and pulled away from the dissolving sample region 34 forms a stream of eluate. The composition of the eluate can comprise the liquid of the eluent and the dissolved material that originates from the embedded sample material forming a dissolved sample material.

The liquid microjunction surface sampling probe can be configured to provide the stream of eluate while maintaining a liquid microjunction interface between a proximal surface of the liquid microjunction surface sampling probe and the thin hydrophobic layer covering the sample in the absorptive layer 20. The proximal surface of the liquid microjunction surface sampling probe can be the end surface of the housing or the outer tube that surrounds the annular capillary that can be placed close to the surface of the absorptive layer 20 during the extraction step. The liquid microjunction interface can be formed between the liquid extraction surface sampling probe and the top surface of the absorptive layer 20 over the dissolving sample region 34. During the operation of the liquid extraction surface sampling probe, the embedded sample material forming a dissolved sample material can be extracted from the dissolving sample region. Alternately, the liquid extraction surface sampling probe can be a sealing surface sampling probe (SSSP).

The liquid extraction surface sampling probe can include at least one inlet (not shown) for letting in the liquid, the stream of eluent, and an outlet (not shown) for letting out the stream of eluate. The inlet can be contiguously connected to the annular capillary through which the eluent can flow toward the absorptive layer 20. The outlet can be contiguously connected to the inner capillary through which the stream of eluate can flow. The end of the inner capillary can be the outlet dispensing into an atmospheric pressure ionization source of a mass spectrometer.

In various embodiments, at least one device 40 can be configured to dispense a liquid onto the sample assembly and also withdraw the dissolved sample material from the sample assembly. In various embodiments, at least a first device can be configured to dispense a liquid onto the sample assembly, and a second device can be configured to extract the dissolved sample material from the sample assembly (10, 20). The first device and the second device can be two distinct pieces that move independently, or they can be mounted on a same probe that can approach the top surface of the sample assembly (10, 20) before operation.

In various embodiments, at least one device can be configured to pneumatically generate a stream of charged droplets onto the sample assembly, similar to the device shown in FIG. 1A. The high velocity charged droplets can momentarily contact the sample material on or embedded in the sample surface and can dissolve the sample material. The charged droplets can extract, in a fashion similar to the microliquid junction, the dissolved sample material from the sample surface and can rebound from the sample surface into an ionization device.

Figure 3D:
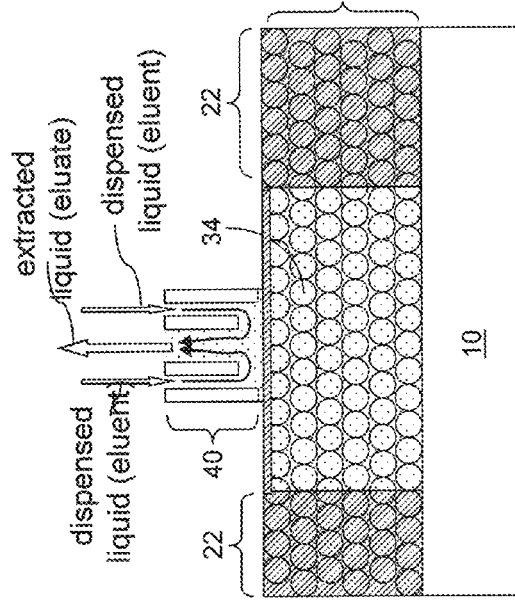
FIG. 3D schematically illustrates a cross-sectional view of the hydrophobic treated surface and sample and the proximal end of the liquid microjunction surface sampling probe after the operation of the sampling probe in accordance with various embodiments of the applicant's teachings.

Referring to FIG. 3D, in various embodiments according to the applicant's teachings, a schematic cross-sectional view of the sample assembly (10, 20) and the proximal end of the at least one device 40 are shown after the extraction operation.

The absorptive layer 20 can include an analyzed area 31 laterally contacting the hydrophobic peripheral portion 22. The extent of the lateral diffusion of the liquid can be limited by the hydrophobic peripheral portion 22 that laterally surrounds or otherwise laterally confines the liquid within the dissolving sample region 34 during the extraction operation. Therefore, once the extraction operation is complete, the entirety of the analyzed area can be substantially free of any foreign material, i.e. can have substantially the same composition as the original material of the absorptive layer 20 before the sample region 30 is formed therein.

Figure 4B:
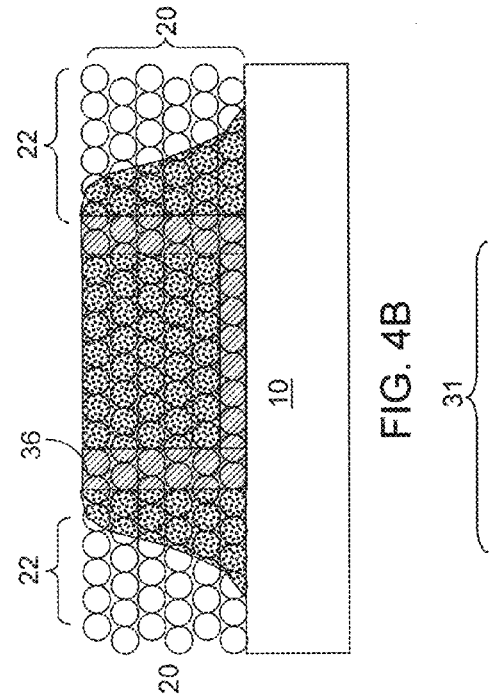
FIG. 4B schematically illustrates a cross-sectional view of a hydrophilic adsorptive layer with hydrophobic barriers after sample is deposited and embedded. Hydrophobic barriers on sides and bottom prevent diffusion of sample and extraction solvent over the sides and out the bottom in accordance with various embodiments of the applicant's teachings.
Figure 4D:
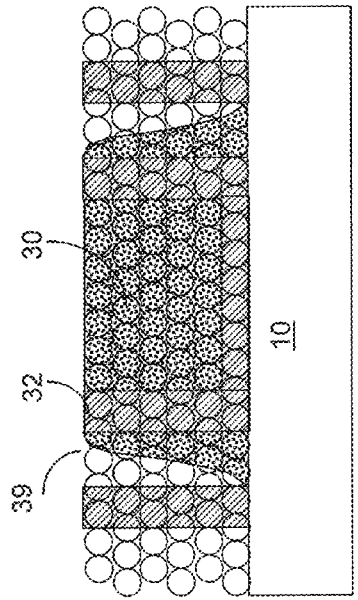
FIG. 4D schematically illustrates a cross-sectional view of a hydrophilic adsorptive layer with excessive sample deposited and embedded. Hydrophobic barriers on the bottom and alternating hydrophobic barriers and hydrophilic side overflow moats prevent lateral diffusion of extraction solvent and maintain a constant volume of sample in the inner sampling region when inner region is overfilled with sample in accordance with various embodiments of the applicant's teachings.
Figure 4A:
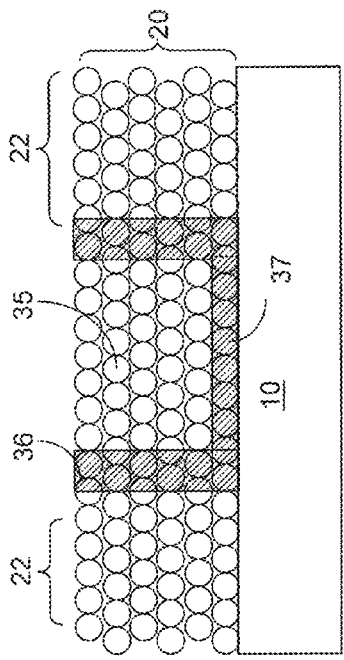
FIG. 4A schematically illustrates a cross-sectional view of a hydrophilic adsorptive layer with hydrophobic barriers prior to depositing and embedding the sample. Hydrophobic barriers on sides and bottom prevent diffusion of sample and extraction solvent over the sides and out the bottom in accordance with various embodiments of the applicant's teachings.
Figure 4C:
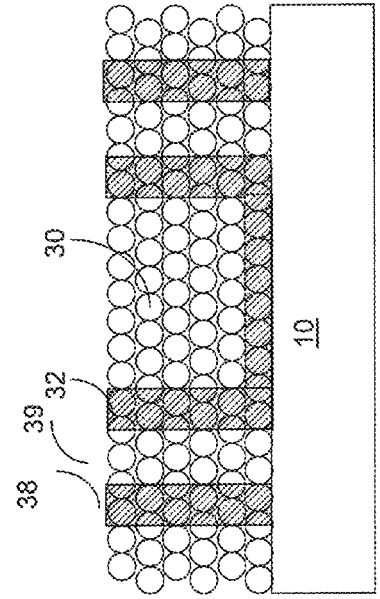
FIG. 4C schematically illustrates a cross-sectional view of a hydrophilic adsorptive layer prior to depositing and embedding the sample. Hydrophobic barriers on the bottom and alternating hydrophobic barriers and hydrophilic side overflow moats prevent lateral diffusion of extraction solvent and maintain a constant volume of sample in the inner sampling region when inner region is overfilled with sample in accordance with various embodiments of the applicant's teachings.

In another embodiment in FIGS. 4A-D, in various embodiments according to the applicant's teachings, a sample well 35 can be formed within the adsorptive material before the sample is added, for example, by patterning layers of wax into side barriers 36 and a bottom barrier 37 as shown in FIG. 4A. When sample is added to the well, it can fill to a constant volume as shown in FIG. 4B and excess sample can spill over the barrier spreading into adjacent adsorptive areas. A constant analysis volume can be obtained when excess sample is available and accurate pipetting of sample is not practical. In FIG. 4C, in various embodiments according to the applicant's teachings, an additional hydrophobic barrier 38 can surround the sampling area creating an adsorptive moat 39. As shown in FIG. 4D, in various embodiments according to the applicant's teachings, when excess sample overflows out of the sample well 30, it can be contained and prevented from spreading to other regions of the adsorptive paper by the moat 39.

Referring to FIGS. 5A-5E, in various embodiments according to the applicant's teachings, the at least one device 40 in FIGS. 3C and 3D can be replaced with a set of devices configured to dispense a liquid onto a sample assembly and to extract or retrieve the liquid from the sample assembly. A plurality of sample assemblies can be analyzed sequentially in various embodiments.

In various aspects, the at least one device can dispense a liquid onto a sample assembly and extract the liquid from the sample assembly simultaneously or with a time interval between the dispensation and the extraction. Further, the at least one device can dispense a liquid onto the sample assembly continuously or intermittently. Likewise, the at least one device can extract the liquid from the sample assembly continuously or intermittently.

At least one exposed well can be filled with a liquid, which can be an extraction solvent, to be used for the extraction of dissolved materials from a sample region in the sample assembly. In operation, to begin the surface sampling process, the robotic arm picks up a conductive pipette tip and moves the tip to a position above the well containing the extraction solvent as shown in FIG. 5A. The tip can be lowered into the well, and the liquid can be aspirated into the tip as shown in FIG. 5B.

Then, the pipette tip can be positioned above the sample region of the sample assembly (which corresponds to the sample region 30 in FIG. 2C) to be sampled. A specific volume of the liquid can be dispensed onto the sample from the tip. The liquid can be dispensed without breaking a liquid junction between the pipette tip and surface of the sample region of the sample assembly as shown in FIG. 5C. The liquid can be confined within the sample region; see the sample region 30 in FIG. 2C, due to the presence of the hydrophobic peripheral portion 22 without being absorbed into a foreign-material-free absorptive portion 20A (See FIG. 2C). The diameter of such a liquid junction can be on the order of the dimension of the pipette tip, which is typically about 1 mm in diameter. The distance between the tip and the surface, and the volumes aspirated and dispensed can be optimized for each individual surface.

The solution containing a dissolved sample material subsequently can be aspirated back into the tip of the pipette as shown in FIG. 5D. The collected liquid, the sample solution, can be sprayed through a nanospray nozzle as shown in FIG. 5E. If a mass spectrometer is provided at the nozzle of the nanospray, the mass spectrometric response of the analyte of interest can be collected, for example, using selected reaction monitoring (SRM).

The robotic arm can withdraw from the well and engage the pipette tip to the back of a nanospray chip, which is an electrospray ionization (ESI) chip. This chip contains microfabricated nozzles to generate nanoelectrospray ionization of liquid samples at flow rates of 20-500 nl/min. The nanoelectrospray can be initiated by applying the appropriate high voltage to the pipette tip and gas pressure on the liquid. If necessary, each nozzle and pipette tip can be used only once to eliminate any possibility of sample-to-sample carryover. The mechanical components of the at least one device 40 of this embodiment are described in Vilmoz Kertesz and Gary J. Van Berkel, "Fully Automated Liquid Extraction-based Surface Sampling and Ionization Using a Chip-based Robotic Nanoelectrospray Platform," *J. Mass. Spectrom*. Vol. 45, Issue 3, Pages 252-260 (2009).

EXAMPLES

Figure 6:
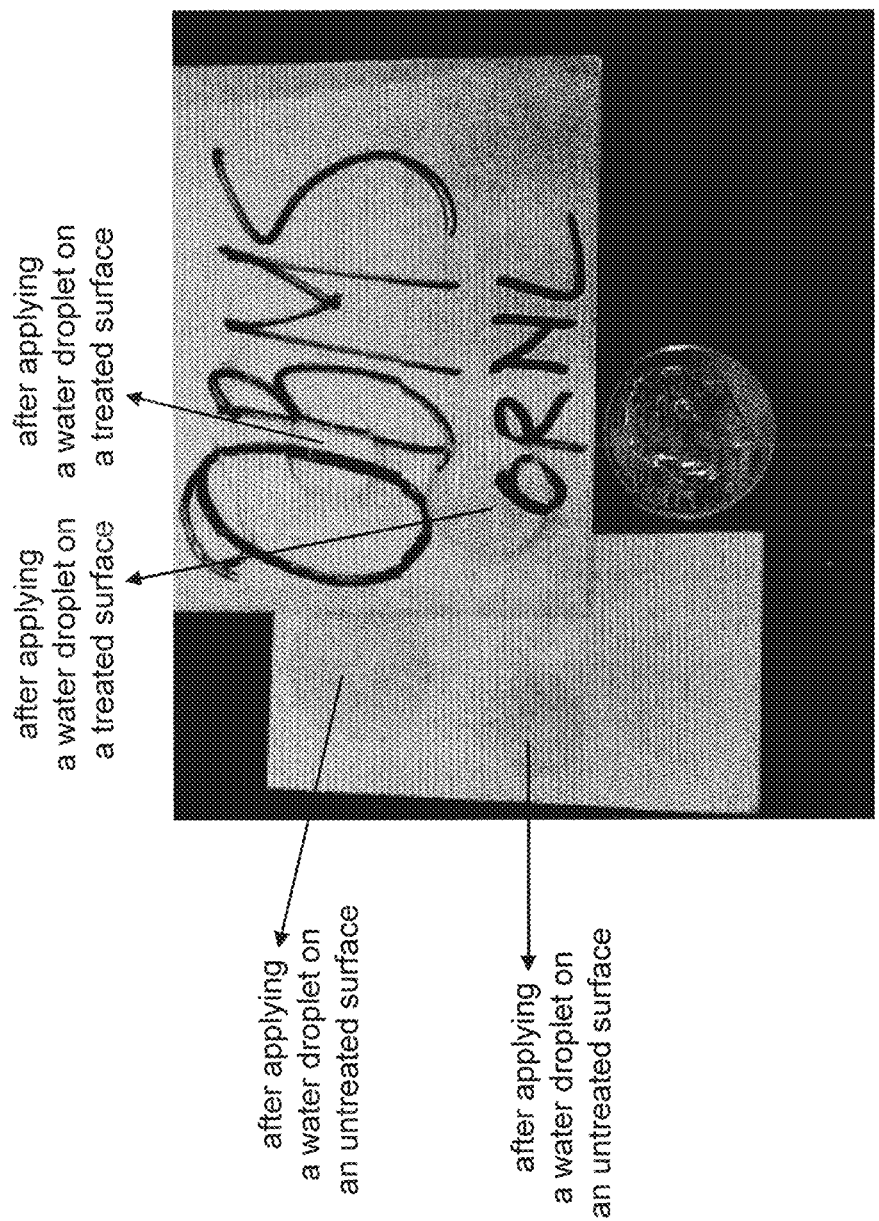
FIG. 6 shows an annotated picture of absorbed water droplets on an untreated hydrophilic high performance thin layer chromatography normal phase (HPTLC) plate and unabsorbed water droplets on a hydrophobic coated normal phase HPTLC plate in accordance with various embodiments of the applicant's teachings.

Referring to FIG. 6, in a first example, an absorptive layer coated with a hydrophobic material according to the applicant's teachings is compared to an untreated surface. Absorbed water droplets on an untreated hydrophilic high performance thin layer chromatography normal phase (HPTLC) plate are shown as two blurred spots on the left side and unabsorbed water droplets on a hydrophobic-coating treated normal phase HPTLC plate treated with a hydrophobic coating are shown as two water droplets in the middle. The material that provides the hydrophobic coating in this example is silicone. The sample region corresponds to the area including the writing "OBMS" and "ORNL." The hydrophobic coating renders the surface of the hydrophobic-coating treated normal phase HPTLC plate hydrophobic so that the water droplets ball up on the surface instead of being absorbed in the HPTLC plate as shown in the untreated plate.

Figure 7:
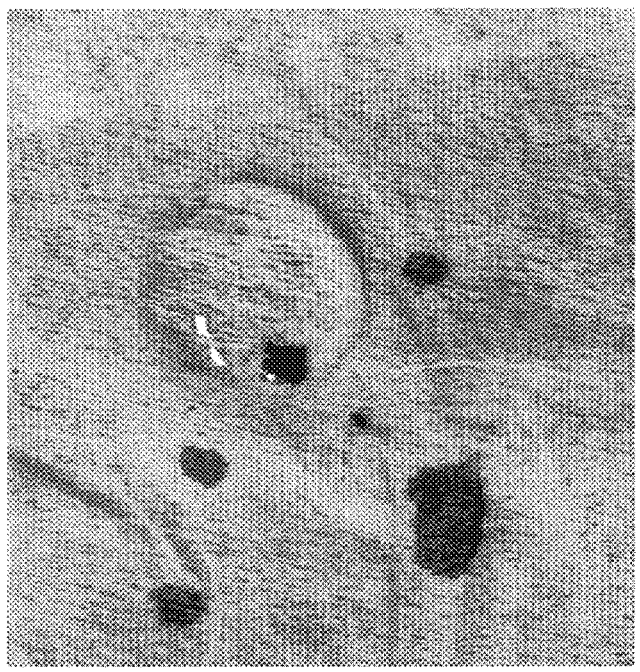
FIG. 7 shows an unabsorbed water droplet on a hydrophobic coated absorbent cleaning tissue (KimWipes®) in accordance with various embodiments of the applicant's teachings.

Referring to FIG. 7, a second example of a hydrophobic-coating-treated absorptive layer according to the applicant's teachings is shown, which is a hydrophobic-coating treated absorbent cleaning tissue (KimWipes®) including several sample regions. The formation of hydrophobic coating peripheral portions and the hydrophobic layers renders the surface of the treated absorbent cleaning tissue hydrophobic. While an attempt to analyze sample regions on an untreated absorbent cleaning tissue by liquid extraction surface sampling probe would have resulted in lateral outward diffusion of the embedded material within the absorbent cleaning tissue, the hydrophobic coating peripheral portions on the hydrophobic-coating-treated absorbent cleaning tissue laterally confine the embedded sample material after a liquid is applied to the sample regions, thereby enabling the liquid extraction surface sampling probe to collect all of the embedded sample material without loss due to lateral outward diffusion within the absorbent cleaning tissue.

Figure 8:
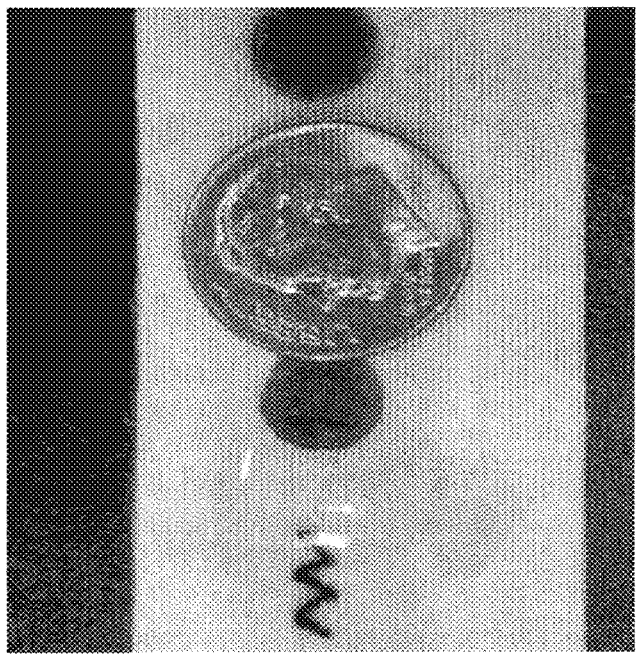
FIG. 8 shows an unabsorbed water droplet on a hydrophobic coated blood spot paper in accordance with various embodiments of the applicant's teachings.

Referring to FIG. 8, a third example of a hydrophobic-coating-treated absorptive layer according to the applicant's teachings is shown, which is a hydrophobic-coating treated blood spot paper. Blood spot paper has been widely used for analysis of blood samples. Due to the absorptive nature of the blood spot paper, however, subjecting an embedded material in a blood spot paper without hydrophobic treatment results in lateral outward diffusion of the embedded material when a liquid is applied, for example, in an attempt to generate an eluate employing a liquid extraction surface sampling probe. The hydrophobic-coating treatment on the blood spot paper renders the surface of the blood spot paper hydrophobic as illustrated by the hydrophobic-coating-treated absorptive layer in FIG. 8. Once the surface of the blood spot paper becomes hydrophobic, the hydrophobic-coating-treated blood spot paper can be subjected to analysis by employing a liquid extraction surface sampling probe without the loss of the embedded sample material, i.e., the blood sample, due to lateral outward diffusion within the blood spot paper.

FIGS. 9A-9G are time-dependent readouts at various m/z settings from a liquid microjunction surface sample probe scan of a post-development treated normal phase HPTLC plate obtained from chromatography on a sample of a goldenseal root extract. The goldenseal root extract is a popular herbal product derived from the goldenseal plant. The goldenseal root extract includes many chemicals such as berberine, hydrasitine, and hydrastinine A high performance thin layer chromatography (HPTLC) run was performed on the goldenseal root extract employing a normal phase HPTLC plate, which is hydrophilic. The normal phase HPTLC plate was subsequently treated with a hydrophobic coating according the methods of the applicant's teachings so that the surface of the normal phase HPTLC plate became hydrophobic. Each band of the normal phase HPTLC was subjected to analysis by a liquid extraction surface sampling probe.

The eluate from each band was subjected to mass spectroscopy and a time dependent reading was taken at a predetermined m/z setting corresponding to the expected composition of each band.

When a first liquid extraction surface sampling run was performed on a first band in the hydrophobic-coating-treated normal phase HPTLC plate, a signal of significant intensity, i.e., a signal well above the background level, was detected at the m/z ratio of 190. FIG. 9A shows the time-dependent readout at the m/z setting of 190 from the first liquid extraction surface sampling run on the first band. The x-axis of FIG. 9A is the time in minutes from the initiation of the first liquid extraction surface sampling run, and the y-axis is the intensity of the peak in arbitrary units as detected by the mass spectrometer. The m/z setting of 190 corresponds to hydrastinine, a compound of the goldenseal root extract.

When a second liquid extraction surface sampling run was performed on a second band in the hydrophobic-coating-treated normal phase HPTLC plate, a signal of significant intensity was detected at the m/z ratio of 384. FIG. 9B shows the time-dependent readout at the m/z setting of 384 from the second liquid extraction surface sampling run on the second band. The x-axis of FIG. 9B is the time in minutes from the initiation of the second liquid extraction surface sampling run, and the y-axis is the intensity of the peak in arbitrary units as detected by the mass spectrometer. The m/z setting of 384 corresponds to hydrastine, a compound of the goldenseal root extract.

When a third liquid extraction surface sampling run was performed on a third band in the hydrophobic-coating-treated normal phase HPTLC plate, a signal of significant intensity was detected at the m/z ratio of 338. FIG. 9C shows the time-dependent readout at the m/z setting of 338 from the third liquid extraction surface sampling run on the third band. The x-axis of FIG. 9C is the time in minutes from the initiation of the third liquid extraction surface sampling run, and the y-axis is the intensity of the peak in arbitrary units as detected by the mass spectrometer. The m/z setting of 338 corresponds to jatrorrhizine, a compound of the goldenseal root extract.

When a fourth liquid extraction surface sampling run was performed on a fourth band in the hydrophobic-coating-treated normal phase HPTLC plate, a signal of significant intensity was detected at the m/z ratio of 352. FIG. 9D shows the time-dependent readout at the m/z setting of 352 from the fourth liquid extraction surface sampling run on the fourth band. The x-axis of FIG. 9D is the time in minutes from the initiation of the fourth liquid extraction surface sampling run, and the y-axis is the intensity of the peak in arbitrary units as detected by the mass spectrometer. The m/z setting of 352 corresponds to berberastine, a compound of the goldenseal root extract.

Figure 9E:
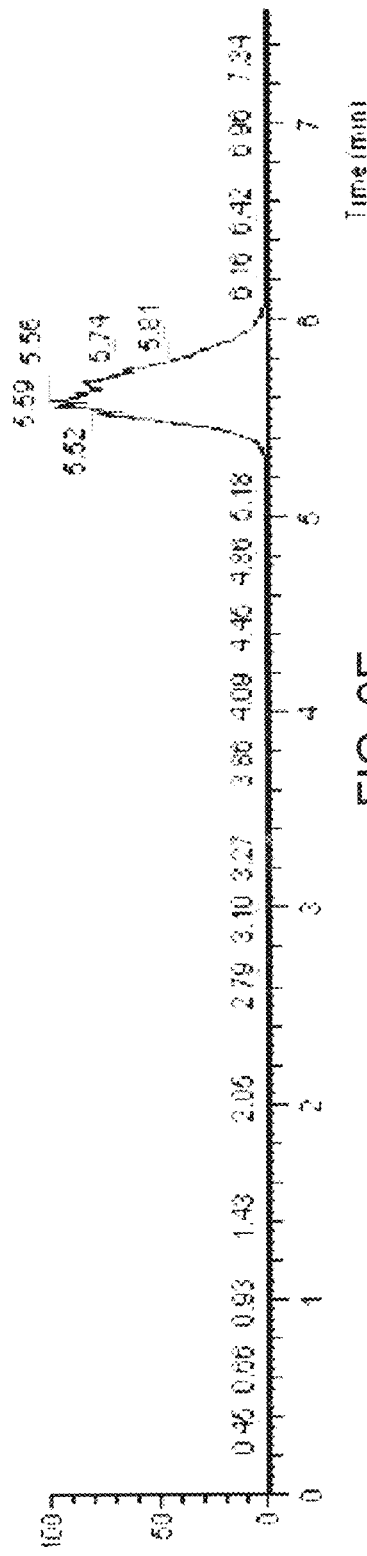
FIG. 9E is a time-dependent readout at m/z setting of 336 (corresponding to berberine) from the liquid microjunction surface sample probe scan of the post-development treated normal phase HPTLC plate obtained from chromatography on a sample of goldenseal root extract coated with a hydrophobic material in accordance with various embodiments of the applicant's teachings.

When a fifth liquid extraction surface sampling run was performed on a fifth band in the hydrophobic-coating-treated normal phase HPTLC plate, a signal of significant intensity was detected at the m/z ratio of 336. FIG. 9E shows the time-dependent readout at the m/z setting of 336 from the fifth liquid extraction surface sampling run on the fifth band. The x-axis of FIG. 9E is the time in minutes from the initiation of the fifth liquid extraction surface sampling run, and the y-axis is the intensity of the peak in arbitrary units as detected by the mass spectrometer. The m/z setting of 336 corresponds to berberine, a compound of the goldenseal root extract.

Figure 9F:
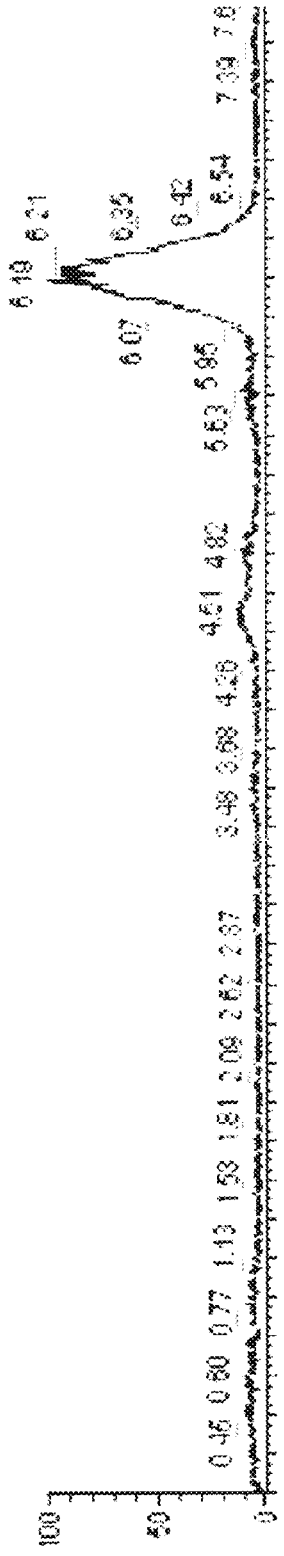
FIG. 9F is a time-dependent readout at m/z setting of 370 (corresponding to canadaline) from the liquid microjunction surface sample probe scan of the post-development treated normal phase HPTLC plate obtained from chromatography on a sample of the goldenseal root extract coated with a hydrophobic material in accordance with various embodiments of the applicant's teachings.

When a sixth liquid extraction surface sampling run was performed on a sixth band in the hydrophobic-coating-treated normal phase HPTLC plate, a signal of significant intensity was detected at the m/z ratio of 370. FIG. 9F shows the time-dependent readout at the m/z setting of 370 from the sixth liquid extraction surface sampling run on the sixth band. The x-axis of FIG. 9F is the time in minutes from the initiation of the sixth liquid extraction surface sampling run, and the y-axis is the intensity of the peak in arbitrary units as detected by the mass spectrometer. The m/z setting of 370 corresponds to canadaline, a compound of the goldenseal root extract.

Figure 9G:
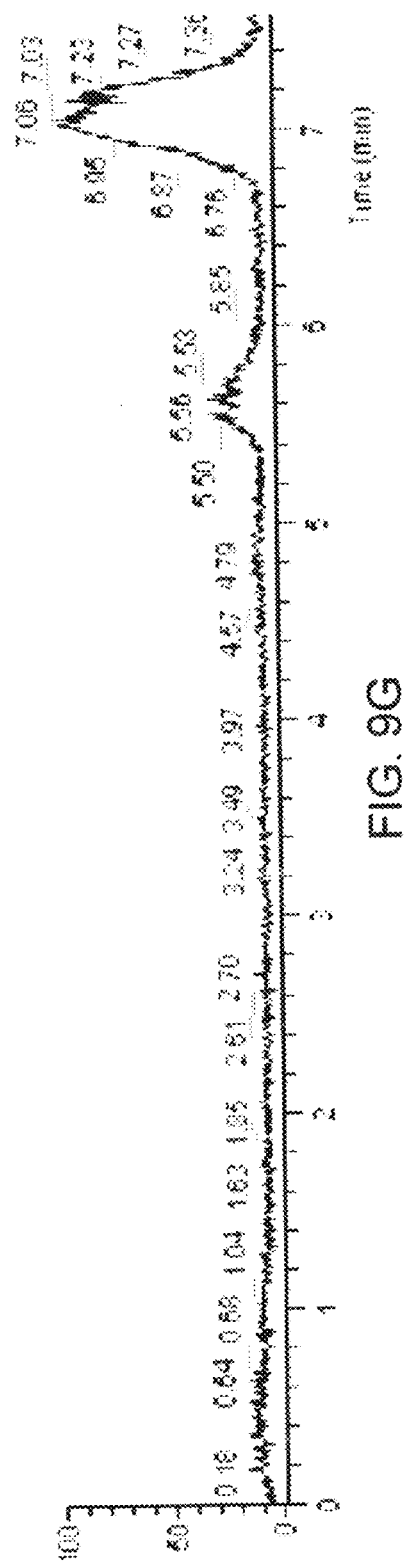
FIG. 9G is a time-dependent readout at m/z setting of 340 (corresponding to tetrahydrobeberine) from the liquid microjunction surface sample probe scan of the post-development treated normal phase HPTLC plate obtained from chromatography on a sample of goldenseal root extract coated with a hydrophobic material in accordance with various embodiments of the applicant's teachings.

When a seventh liquid extraction surface sampling run was performed on a seventh band in the hydrophobic-coating-treated normal phase HPTLC plate, a signal of significant intensity was detected at the m/z ratio of 340. FIG. 9G shows the time-dependent readout at the m/z setting of 340 from the seventh liquid extraction surface sampling run on the seventh band. The x-axis of FIG. 9G is the time in minutes from the initiation of the seventh liquid extraction surface sampling run, and the y-axis is the intensity of the peak in arbitrary units as detected by the mass spectrometer. The m/z setting of 340 corresponds to tetrahydrobeberine, a compound of the goldenseal root extract.

In summary, each liquid extraction surface sampling run on a band in the hydrophobic-coating-treated normal phase HPTLC plate extracted the chemical of the band successfully without extracting materials of another band or contaminating another band by pushing out the material of the band outward. The containment of the liquid, i.e., the eluting solvent within each sample area of an individual band can be effected by the presence of the hydrophobic peripheral portions around each band. Thus, the hydrophobic coating method of the applicant's teachings can be employed in combination with a liquid extraction surface sampling probe to provide enhanced sensitivity, reduced sample loss, and elimination of contamination of other sample regions when multiple sample regions are present on the same absorptive layer.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While the applicant's teachings have been particularly shown and described with reference to specific illustrative embodiments, it should be understood that various changes in form and detail may be made without departing from the spirit and scope of the teachings. Therefore, all embodiments that come within the scope and spirit of the teachings, and equivalents thereto, are claimed. The descriptions and diagrams of the methods of the applicant's teachings should not be read as limited to the described order of elements unless stated to that effect.

While the applicant's teachings have been described in conjunction with various embodiments and examples, it is not intended that the applicant's teachings be limited to such embodiments or examples. On the contrary, the applicant's teachings encompass various alternatives, modifications, and equivalents, as will be appreciated by those of skill in the art, and all such modifications or variations are believed to be within the sphere and scope of the applicant's teachings.

The invention claimed is:

1. A system for extracting a sample analyte with a liquid, comprising:
    a sample collection device comprising a continuous portion of porous sample collection material, the porous sample collection material being capable of absorbing the sample such that the sample penetrates below the surface of the porous sample collection material;
    predetermined regions of the continuous porous sample collection material defining barrier regions for containing the flow of sample extraction liquid;
    a hydrophobic material coating the porous sample collection material in the barrier regions for containing the flow of sample extraction liquid, the hydrophobic material comprising patterns in the porous sample collection material forming sample wells prior to depositing the sample, the sample wells being non-reactive with the analyte;
    a liquid extraction surface sampling probe for applying the extraction liquid to the surface of the porous sample collection material, and for withdrawing extraction liquid containing extracted sample from the same surface of the porous sample collection material through the liquid extraction surface sampling probe; and
    further comprising ionizing the extracted dissolved sample material downstream of the porous material and the liquid extraction surface sampling probe.

2. The system of claim 1 wherein the porous sample collection material comprises a hydrophilic material.

3. The system of claim 1 wherein the porous sample collection material is selected from a group consisting of paper, fabric, porous ceramic material and a combination thereof.

4. The system of claim 1 wherein a substrate provides mechanical support to the porous sample collection material.

5. The system of claim 1 wherein the hydrophobic material is selected from a group consisting of silicone, fluorinated alkane, and waxes.

6. The system of claim 1 further comprising hydrophobic barriers and moats to contain overflow of the sample from the sample wells.

7. The system of claim 1 wherein a hydrophobic layer is provided over the porous sample collection material containing the sample.

8. The system of claim 1 wherein the hydrophobic material comprises a solid phase at 293.15 K.

9. The system of claim 1 wherein the sample comprises a biological material.

10. The system of claim 9 wherein the sample comprises blood.

11. The system of claim 1 wherein the liquid comprises a solvent that dissolves the sample.

12. The system of claim 1 wherein a device for ionizing the dissolved sample material is selected from the group consisting of an electrospray ionization device, an atmospheric chemical ionization device, an inductively coupled plasma ionization device, and an atmospheric photo ionization device.

13. The system of claim 12 wherein the ionized dissolved sample material is analyzed by a mass spectrometer.

14. A method of extracting a sample analyte from a sample collection material having a surface, the method comprising the steps of:
    defining barrier regions in the sample collection material;
    applying a hydrophobic material to the porous sample collection material at the barrier regions to impede the flow of extraction liquid and sample through the barrier regions, the hydrophobic material defining patterns in the porous sample collection material forming sample wells prior to depositing the sample, the sample wells being non-reactive with the analyte;
    depositing a sample on the surface of the porous sample collection material, the sample penetrating below the surface of the porous collection material;
    dispensing a sample extraction liquid on the surface of the sample collection material with a liquid extraction surface sampling probe to dissolve the sample to form a dissolved sample analyte, the barrier regions retarding the spread of the extraction liquid through the porous sample collection material;
    extracting the dissolved sample analyte from the same sample surface through the liquid extraction surface sampling probe, the extraction liquid including the extracted sample analyte being withdrawn by the negative pressure from porous sample collection material through the liquid extraction surface sampling probe; and
    further comprising ionizing the extracted dissolved sample analyte downstream of the porous material and the surface sampling probe.

15. The method of claim 14 wherein the porous sample collection material comprises a hydrophilic material.

16. The method of claim 14 wherein the porous sample collection material is selected from a group consisting of paper, fabric, porous ceramic material and a combination thereof.

17. The method of claim 14 wherein a mechanical support is provided to the porous sample collection material by a substrate.

18. The method of claim 14 wherein the hydrophobic material is selected from a group consisting of silicone, fluorinated alkane, and waxes.

19. The method of claim 14 further providing hydrophobic barriers and moats to contain overflow of the sample from the sample wells.

20. The method of claim 14 wherein a hydrophobic layer is provided over the region of the porous sample collection material containing the sample.

21. The method of claim 14 wherein the hydrophobic material comprises a solid phase at 293.15 K.

22. The method of claim 14 wherein the sample is embedded in the porous sample collection material.

23. The method of claim 14 wherein the sample comprises a biological material.

24. The method of claim 23 wherein the sample comprises blood.

25. The method of claim 14 wherein the liquid comprises a solvent that dissolves the sample.

26. The method of claim 1 wherein a device for ionizing the dissolved sample material is selected from the group consisting of an electrospray ionization device, an atmospheric chemical ionization device, an inductively coupled plasma ionization device, and an atmospheric photo ionization device.

27. The method of claim 26 wherein the ionized dissolved sample material is analyzed by a mass spectrometer.

28. The system of claim 1, wherein the barrier regions are at least in part below a surface of the porous sample collection material.

29. The system of claim 28, wherein the barrier regions define a plurality of sample wells in the sample collection material.

30. The system of claim 29, wherein barrier regions define side barrier regions and a connected bottom barrier region.

31. The system of claim 30, wherein the side barrier regions of the wells are surrounded by uncoated porous sample collection material to define an overflow region.

32. The system of claim 31, wherein the overflow region is surrounded by a barrier region defining moat walls for confining solvent overflowing from a sample well within the overflow region.

33. The system of claim 1, wherein the barrier region is at a surface of the sample collection material.

34. The method of claim 14, wherein the barrier regions are at least in part below the surface of the porous sample collection material, the hydrophobic material penetrating the porous sample collection material below the surface to coat porous sample collection material in the barrier regions below the surface.

* * * * *